(12) United States Patent
Sauder et al.

(10) Patent No.: US 10,451,600 B2
(45) Date of Patent: Oct. 22, 2019

(54) SOIL SAMPLING APPARATUS, SYSTEM AND METHOD

(71) Applicant: 360 Yield Center, LLC, Morton, IL (US)

(72) Inventors: Gregg A. Sauder, Tremont, IL (US); Tony Carbaugh, Washington, IL (US); Rhett W. Schildroth, North Liberty, IA (US)

(73) Assignee: 360 Yield Center, LLC, Morton, IL (US)

(*) Notice: Subject to any disclaimer, the term of this patent is extended or adjusted under 35 U.S.C. 154(b) by 185 days.

(21) Appl. No.: 15/231,756

(22) Filed: Aug. 8, 2016

(65) Prior Publication Data

US 2017/0045489 A1    Feb. 16, 2017

Related U.S. Application Data

(60) Provisional application No. 62/203,375, filed on Aug. 10, 2015.

(51) Int. Cl.
| | |
|---|---|
| *G01N 1/08* | (2006.01) |
| *G01N 33/24* | (2006.01) |
| *G01N 1/28* | (2006.01) |
| *E02D 1/04* | (2006.01) |

(52) U.S. Cl.
CPC ............... *G01N 33/24* (2013.01); *E02D 1/04* (2013.01); *G01N 1/08* (2013.01); *G01N 1/28* (2013.01); *G01N 2033/245* (2013.01)

(58) Field of Classification Search
CPC .... G01N 33/24; G01N 2033/245; G01N 1/28; G01N 1/08; E02D 1/04; E02D 1/025

USPC ..................... 73/863–864.91, 866
See application file for complete search history.

(56) References Cited

U.S. PATENT DOCUMENTS

| | | | |
|---|---|---|---|
| 4,922,763 A * | 5/1990 | Ashworth | E21B 7/001 175/58 |
| 5,668,719 A | 9/1997 | Bobrov et al. | |
| 8,144,319 B2 | 3/2012 | Preiner et al. | |
| 8,286,857 B2 | 10/2012 | Covely | |
| 8,325,336 B2 | 12/2012 | Preiner et al. | |
| 8,472,023 B2 | 6/2013 | Preiner et al. | |
| 8,472,024 B2 | 6/2013 | Preiner et al. | |
| 8,477,295 B2 | 7/2013 | Preiner et al. | |
| 9,255,878 B2 | 2/2016 | Preiner et al. | |
| 2005/0150160 A1 | 7/2005 | Norgaard et al. | |
| 2005/0172733 A1* | 8/2005 | Drummond | A01B 79/005 73/864.41 |

(Continued)

FOREIGN PATENT DOCUMENTS

| | | | |
|---|---|---|---|
| AU | 2011320873 B2 | | 9/2014 |
| CN | 103884553 | * | 6/2014 |

(Continued)

*Primary Examiner* — Robert R Raevis
(74) *Attorney, Agent, or Firm* — Thomas J. Oppoid; Larkin Hoffman Daly & Lindgren. Ltd.

(57) ABSTRACT

A soil sampling apparatus, system and method for creating soil shavings. As the continuous soil shaving chain or other means of creating soil shavings penetrates the soil, soil shavings are discharged through a discharge opening for collection in a canister for analysis of the soil characteristics. In an alternative embodiment, a sensor is positioned to detect soil characteristics as the soil shavings are discharged.

19 Claims, 21 Drawing Sheets

(56) References Cited

U.S. PATENT DOCUMENTS

| | | |
|---|---|---|
| 2009/0164281 A1 | 6/2009 | Norgaard et al. |
| 2012/0103077 A1 | 5/2012 | Koshnick et al. |
| 2013/0247655 A1 | 9/2013 | Preiner et al. |
| 2014/0095074 A1 | 4/2014 | Covely |
| 2014/0345394 A1 | 11/2014 | Schildroth |
| 2014/0365083 A1 | 12/2014 | Covely |
| 2014/0365084 A1 | 12/2014 | Chan et al. |
| 2014/0379228 A1 | 12/2014 | Batcheller et al. |
| 2015/0006212 A1 | 1/2015 | Covely |
| 2016/0018224 A1* | 1/2016 | Isler .................. G01C 21/005 701/25 |

FOREIGN PATENT DOCUMENTS

| | | |
|---|---|---|
| JP | 201675691 A | 5/2016 |
| JP | 201675692 A | 5/2016 |
| WO | 2010129874 A1 | 11/2010 |
| WO | 2010129877 A1 | 11/2010 |
| WO | 2012057929 A1 | 5/2012 |
| WO | 2014177856 A1 | 11/2014 |

\* cited by examiner

| | |
|---|---|
| Farm | New Farm ▽ |
| Field | South Feedlot ▽ |
| Field Analysis | Default Analysis ▽ |
| Sample Number | 2 |
| Sample Depth | 12   Core Length   12 |

Notes

FIG. 20

SOIL SAMPLING APPARATUS, SYSTEM AND METHOD

BACKGROUND

Agricultural production can be unpredictable due to variability in relationships and patterns within a field for certain agronomic characteristics such as soil properties, topography, climate and other agronomic factors. Advancements in testing agronomic characteristics, through remote sensing, such as the use of unmanned aerial vehicles (UAVs) and on-demand soil sampling, have created the possibility to assess these agronomic characteristic variations in real or near real-time and create appropriate management strategies in real or near real-time. Such management strategies have the potential to optimize crop production. However, this potential is highly dependent on the quality of the agronomic characteristics testing and the accuracy of the assessment of these variations.

One way in which agronomic characteristics are tested is through soil sampling. The agricultural industry uses soil samples to determine the nutrient level of soil in fields. Soil sampling and testing provides an estimate of the capacity of the soil to supply adequate nutrients to meet the needs of growing crops. In some instances, the test results are compared to standard response data associated with specific types of crops to estimate the need to supply additional nutrients for optimum crop production. The test results are then used as a basis for profitable and environmentally responsible fertilizer application.

Due to cost and the time consuming nature of the work, a farmer will typically hire a third party to test agronomic characteristics through soil sampling or remote sensing. The third party collects the soil samples and remotely sensed data and sends them to a lab for further analysis. The work is very time consuming, motivating the third party or farmer to cut corners by not getting enough test samples or not getting the test samples from the right locations.

Soil samples are collected according to a grid pattern which divides up a field into cells with each cell representing an area of the field. Grid sampling can be extremely difficult to accomplish when the weather or field conditions are poor, or when obtained during the growing season, the crop is tall or thick, resulting in critical data points not being collected.

A soil sampler uses a soil probe to take a soil core, which is then placed in a container and sent to a lab for soil analysis. The soil samplers then identifies the container to distinguish it from other containers, often by handwriting specific information on each container or by applying a pre-made label to the sample Obtaining soil cores is physically demanding, tedious work. The sampler typically takes hundreds of samples from many soil types, some of which complicate the process of obtaining the soil core by being dense, wet or filled with rocks. Because of the nature of the work, a soil sampler may cheat, taking far too few soil samples or taking the samples in locations based on convenience (e.g., to avoid walking long distances through tall corn or muddy fields) instead of comprehensively.

What is needed then, is a soil sampling apparatus, system and method that reduces the physical demands of soil sampling thereby encouraging a soil sampler to take all necessary samples in the area of interest.

What is further needed is a soil sampling apparatus, system and method that provides a consistent soil sample, i.e., a sample that is sufficiently mixed and macerated, free of large clumps and representative of the soil profile in the area of the interest.

Further, what is needed is a soil sampling apparatus, system and method which collects and isolates the soil sample in a collection container without additional handling or transferring from a soil probe.

What is needed then is a soil sampling apparatus, method and system which collects and contains sample, the sample corresponding to the sampling location or locations and the sampling depth or depths in the area of interest.

BRIEF DESCRIPTION OF THE DRAWINGS

FIG. 20 is an example of a screen shot of mobile device application which captures and displays certain soil parameters automatically during the collection of a soil sample.

DESCRIPTION

Figure 1:
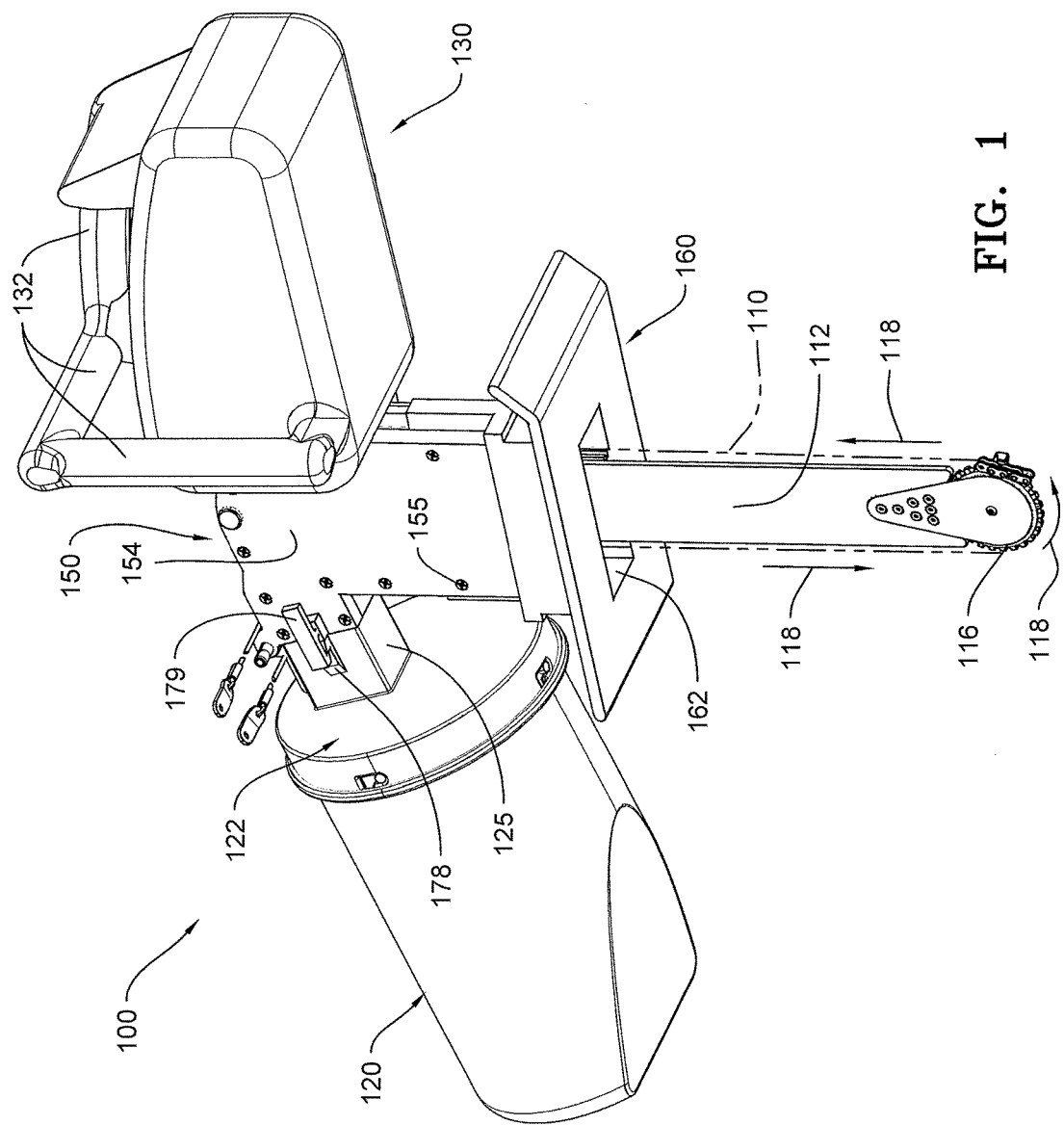
FIG. 1 is a left lower rear perspective view of one embodiment of a soil sampling apparatus.
Figure 2:
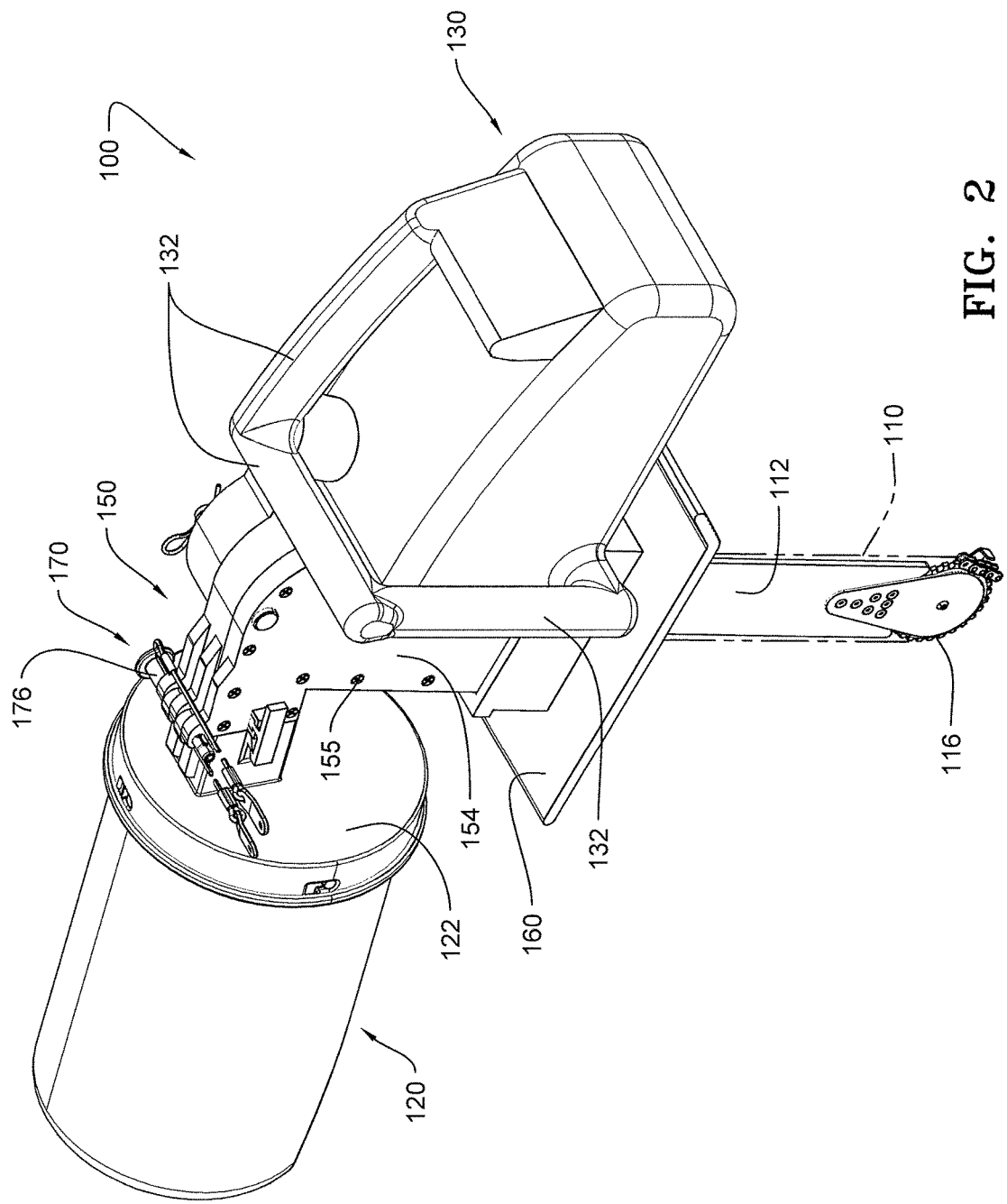
FIG. 2 is a left upper rear perspective view of the soil sampling apparatus of FIG. 1
Figure 3:
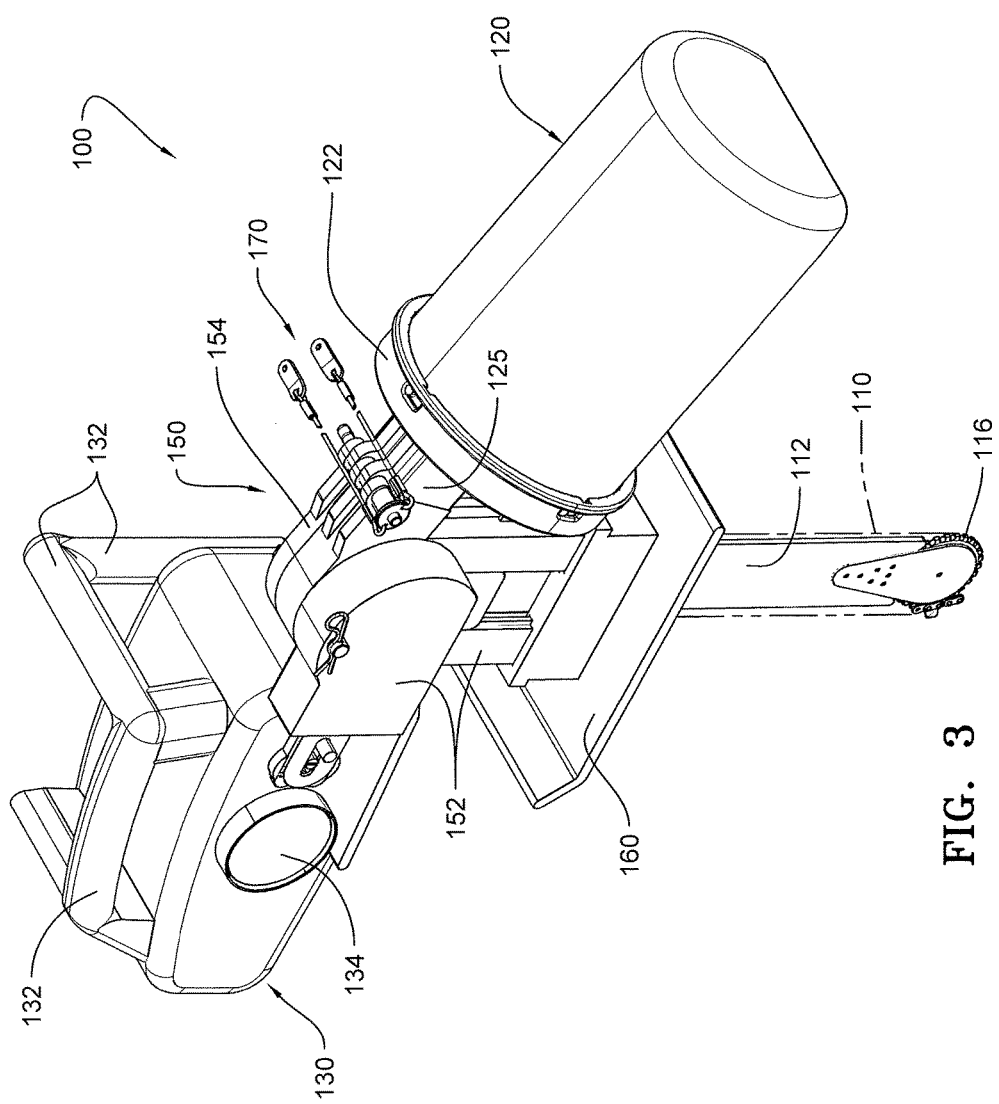
FIG. 3 is a front upper right perspective view of the soil sampling apparatus of FIG. 1.

Referring to the drawing figures, wherein like reference numerals designate the same or corresponding parts throughout the several views, FIGS. 1-7 illustrate one embodiment of a soil sampling apparatus 100 which is substantially similar in construction to a conventional chainsaw but with the chain bar 110 oriented vertically instead of horizontally such that the cutter bar cuts vertically into the soil. One or more canisters 120 collect the soil "shavings" discharged by the rotating soil shaving chain.

Like a conventional chain saw, the apparatus 100 includes a gas powered engine or battery powered motor within the main body 130. The body 130 includes handles 132 for gripping by the user to push the chain bar 110 into the soil during the soil collecting operation (discussed later). Similar to a conventional chainsaw, one of the gripping handles 132 may include a trigger throttle (not shown).

Apart from its orientation with respect to the main body 130, the chain bar 110 is similar to a chain bar of a conventional chain saw and comprises a guidebar 112 with a soil shaving chain 114 that rotates around the guidebar 112. As with a conventional chain saw chain, the soil shaving chain 114 is comprised of a plurality of links with spaced teeth 115.

Figure 7:
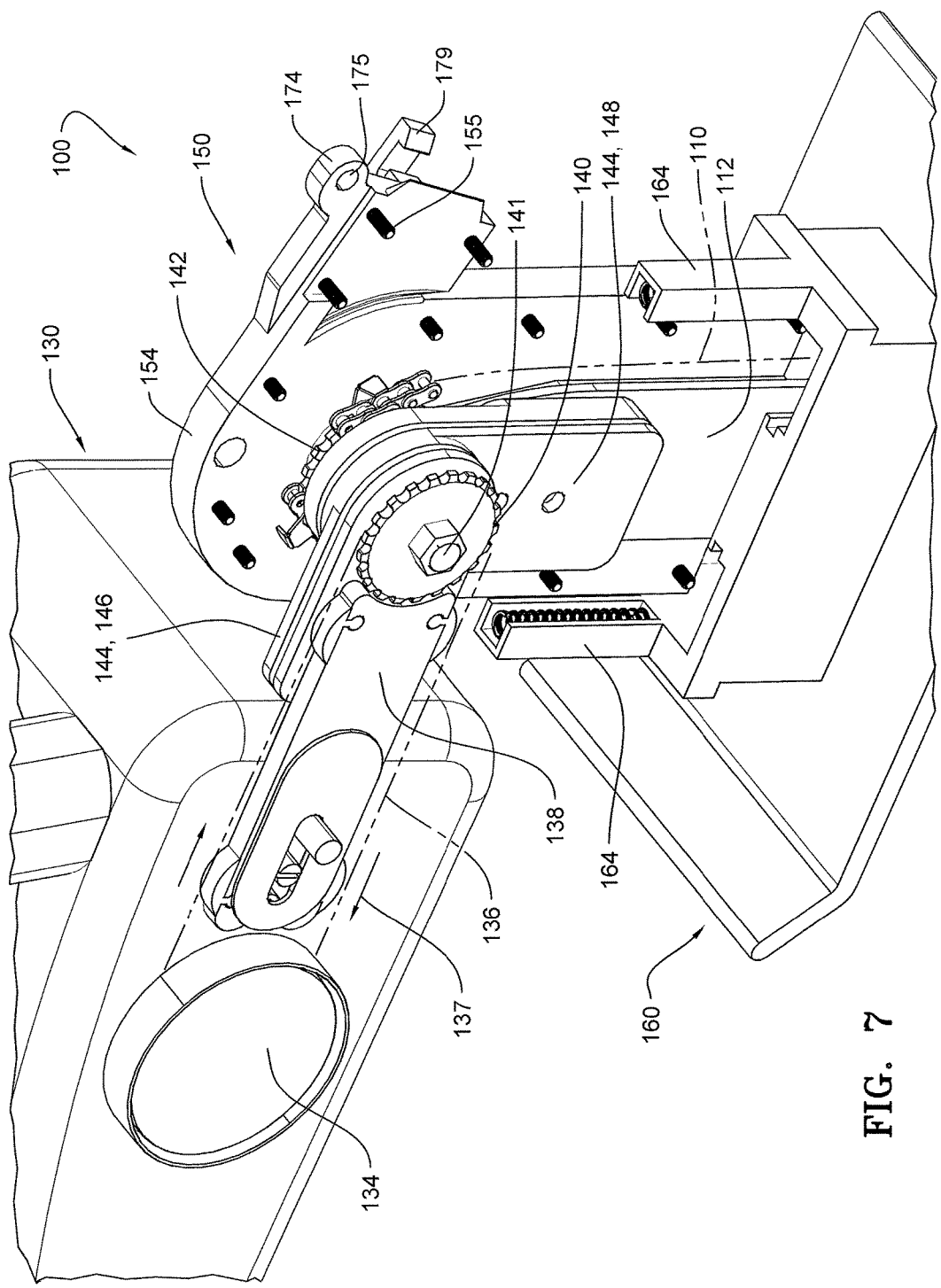
FIG. 7 is an enlarged right side view of the soil sampling apparatus of FIG. 1 with the right housing wall removed to show the interior of the housing.

Also similar to a conventional chainsaw, and as best illustrated in FIG. 7, the soil sampling apparatus 100 includes a drive mechanism 134. The drive mechanism 134 which rotates a drive chain 136 (indicated by phantom line, but see FIG. 16 as an example). The drive chain 136 extends around the drive mechanism 134 and around a horizontal guidebar 138. At the forward end of the horizontal guidebar 138 is a drive chain sprocket 140. The drive mechanism 134 and sprocket 140 cooperate to rotate the drive chain 136 in the direction of arrow 137 as shown in FIG. 7.

Figure 6:
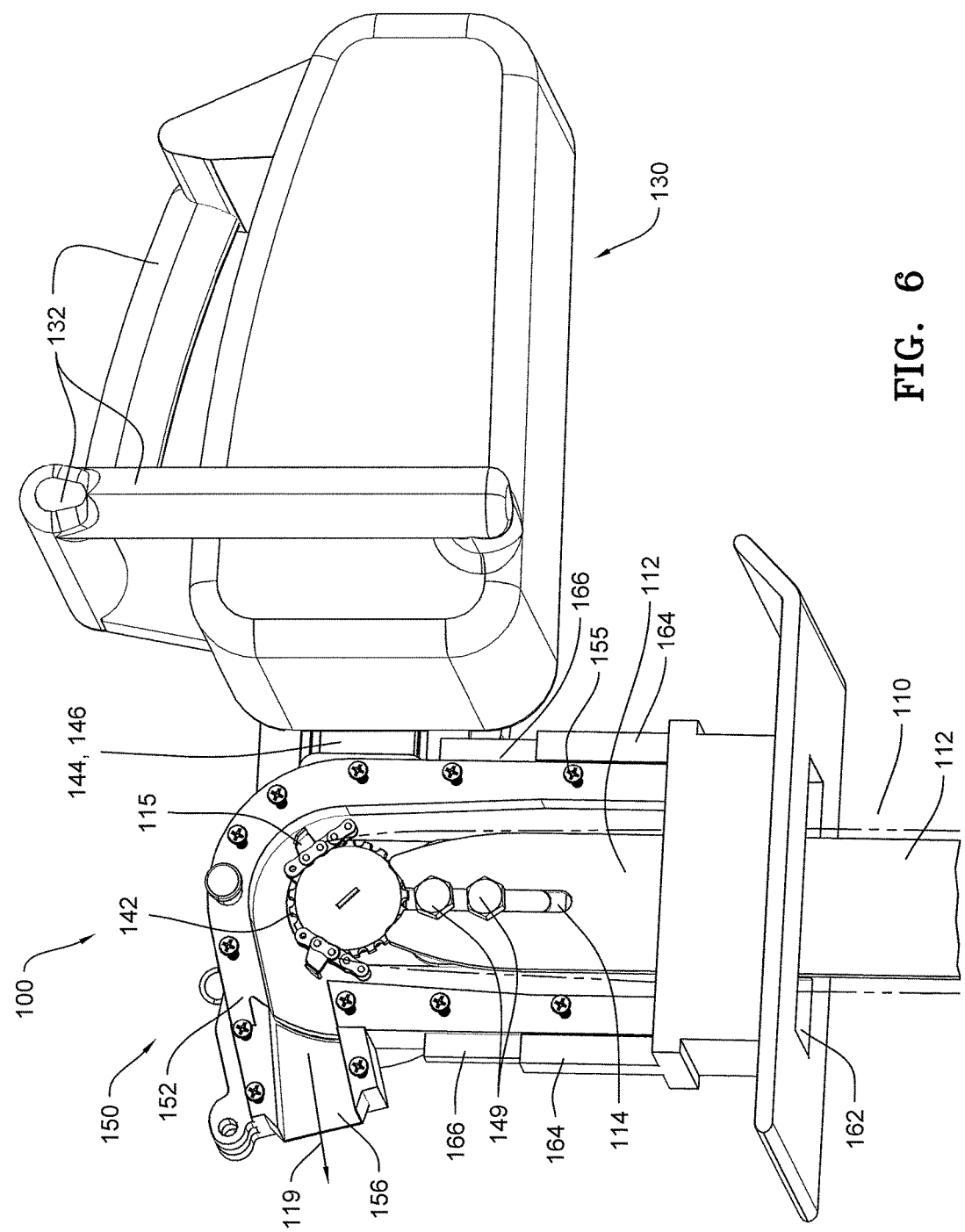
FIG. 6 is an enlarged left side view of the soil sampling apparatus of FIG. 1 with the left housing wall removed to show the interior of the housing.

A drive shaft 141 rotatably couples the drive chain sprocket 140 with an upper shaving chain sprocket 142 (FIG. 6). The soil shaving chain 114 extends around the upper shaving chain sprocket 142 and around a lower shaving chain idler sprocket 116 at the opposite end of the vertical guide bar 112. The sprockets 142, 116 cooperate to rotate the shaving chain 114 around the guidebar 112 in the direction of arrow 118 (see FIGS. 1 and 7).

The drive shaft 141 is rotatably supported from the main body 130 by an L-shaped bracket 144, with the horizontal leg 146 of the L-shaped bracket 144 rigidly secured to the main body 130, such as by a threaded connector (not shown). The vertical leg 148 of the L-shaped bracket 144 serves as a mount for the vertical guidebar 112 of the cutter bar 110. The vertical leg 148 of the L-shaped bracket threadably receives the threaded connectors 149 which extend through a vertical slot 114 in the vertical guidebar 112 thereby frictionally vertically and laterally restraining the guidebar 112 with respect to the L-shaped bracket 144.

As best shown in FIG. 6, the upper end of the vertical guidebar 112, the drive chain sprocket 140 and the upper shaving chain sprocket 142 are received within a housing 150, comprising right and left side panels 152, 154 and spaced apart by peripheral wall 153 which together define an enclosure with an open bottom through which the cutter bar 110 extend. The side panels 152, 154 may be removable from one another for servicing and cleaning by removing threaded connectors 155 securing them together. The housing 150 may be supported from the L-shaped bracket 144. In FIG. 6, the left housing panel 154 is removed to show the interior of the housing 150. Similarly, in FIG. 7, the right housing panel 152 is removed to shown the interior of the housing 150.

A foot plate 160 is supported from the base of the housing 150. The foot plate 160 includes an opening 162 through which the chain bar 110 extends. Foot slide channels 164 cooperate with a rib 166 on the housing 150 permitting the foot plate 160 to be vertically adjustable with respect to the end of the vertical guidebar 112 thereby enabling the user to set the depth of penetration of the chain bar 110 into the soil (e.g., at 12, 18 or 24 inch depths).

Figure 4:
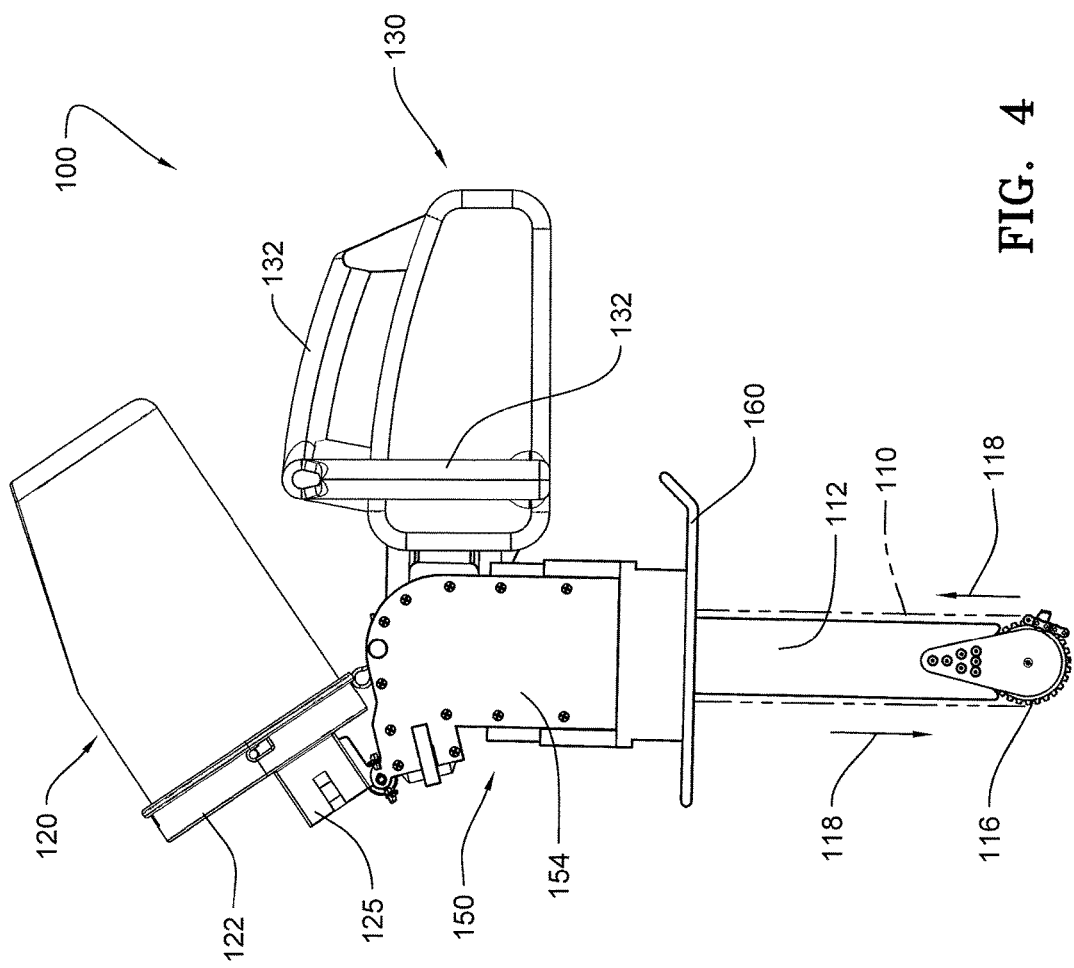
FIG. 4 is a left side elevation view of the soil sampling apparatus of FIG. 1.
Figure 5:
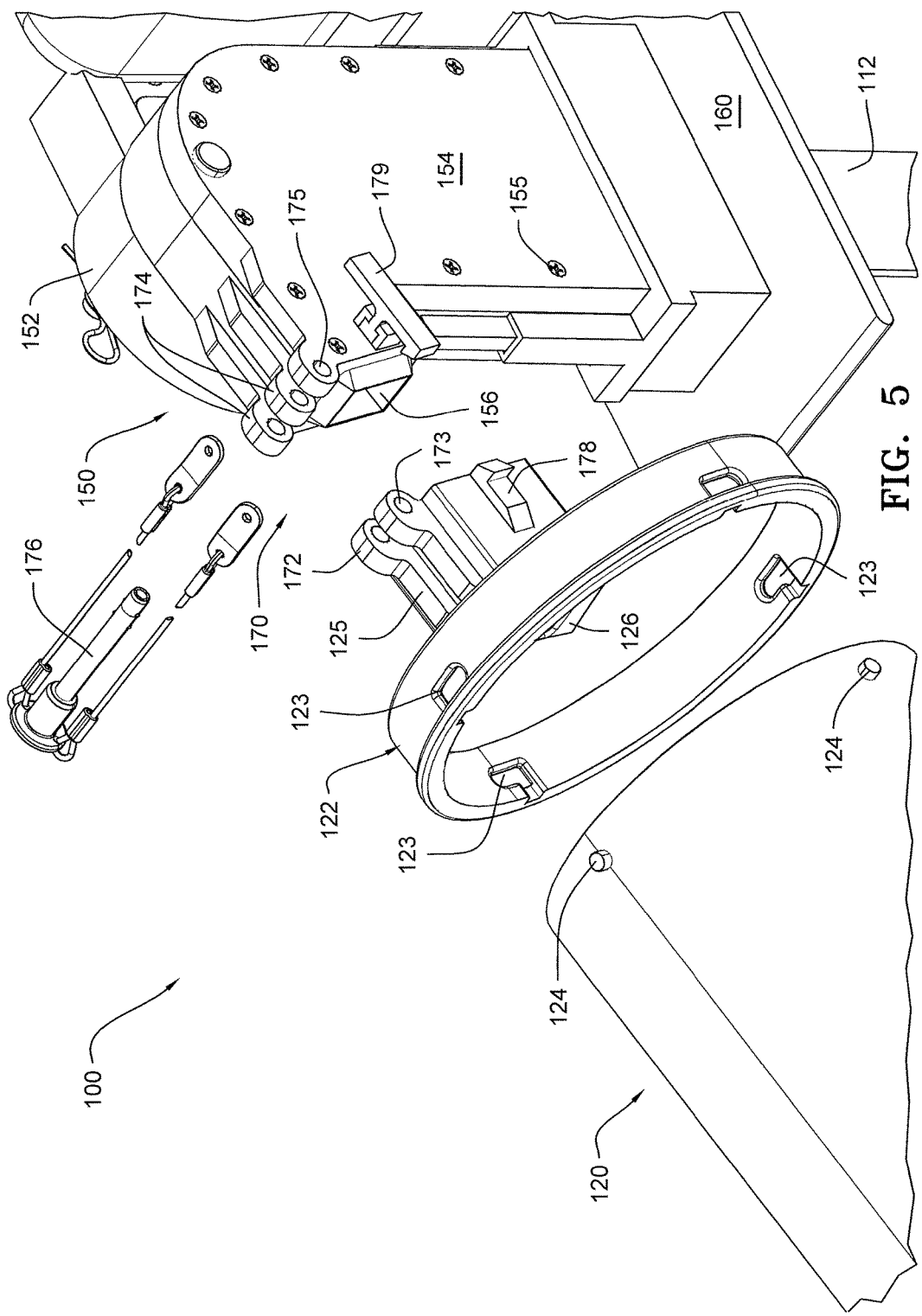
FIG. 5 is an enlarged exploded perspective view of the soil sampling apparatus of FIG. 1.

As best illustrated in FIG. 5, the canister 120 removably attaches to a lid 122. The lid 122 includes a plurality of L-shaped slots 123 which matingly receive pegs 124 extending outwardly from the canister 120 near its upper end. Rotating the canister 120 causes the pegs 124 to engage the transverse leg of the L-shaped slots 123, thereby locking the canister 120 to the lid 122. The lid 122 is, in turn, pivotally attached to the upper end of the housing 150 by a hinge assembly 170 which permits the canister to be pivoted upwardly (see FIG. 4) for reasons discussed later. A rectangular connecting tube 125 extends from the top side of the lid 122. The tube 125 has a passage 126 which extends through the lid 122. The connecting tube 125 aligns with an outlet 156 in the housing 150 permitting the soil shavings discharged by the rotating soil shaving chain 114 to pass through the passage 126 in the lid 122 and into the canister 120 for collection as discussed below.

The hinge assembly 170 comprises mating ears 172, 174 extending from the connecting tube 125 and the housing 150, respectively. The mating ears 172, 174 include apertures 173, 175. A pin 176 extends through the ears 172, 174 and aligned apertures 175, 176 thereby forming the hinged connection between the canister/lid assembly 120, 122 and the housing 150. Locking tabs 178, 179 on the tube 125 and the housing 150 engage one another to securely lock the canister/lid assembly to the housing, so the canister/lid assembly stays in place.

In use, the canister 120 is preferably flipped or rotated up as shown in FIG. 4 allowing the soil shavings to be discharged through the outlet 156 in the housing 150. When the desired penetration depth into the soil is reached, the canister may be flipped or rotated forwardly such that the locking tabs 178, 179 are engaged and the passage 126 through the connecting tube 125 is aligned with the outlet 156 of the housing. By drawing the chain bar 110 rearward as the soil shaving chain 114 rotates, the soil shavings are carried up into the housing 150 by the teeth 115 on the soil shaving chain 114. When the teeth 115 pass over the upper sprocket 142, the soil shavings are flung or discharged in the direction of arrow 119 through the housing outlet 156 and through the passage 126 and into the canister 120.

FIGS. 8-12 illustrate an alternative soil sampling apparatus 200 which is substantially similar to the first embodiment, except for the manner in which the canister is attached to the housing and the use of a lever to direct the soil into the canister rather than the canister pivoting in position.

Figure 8:
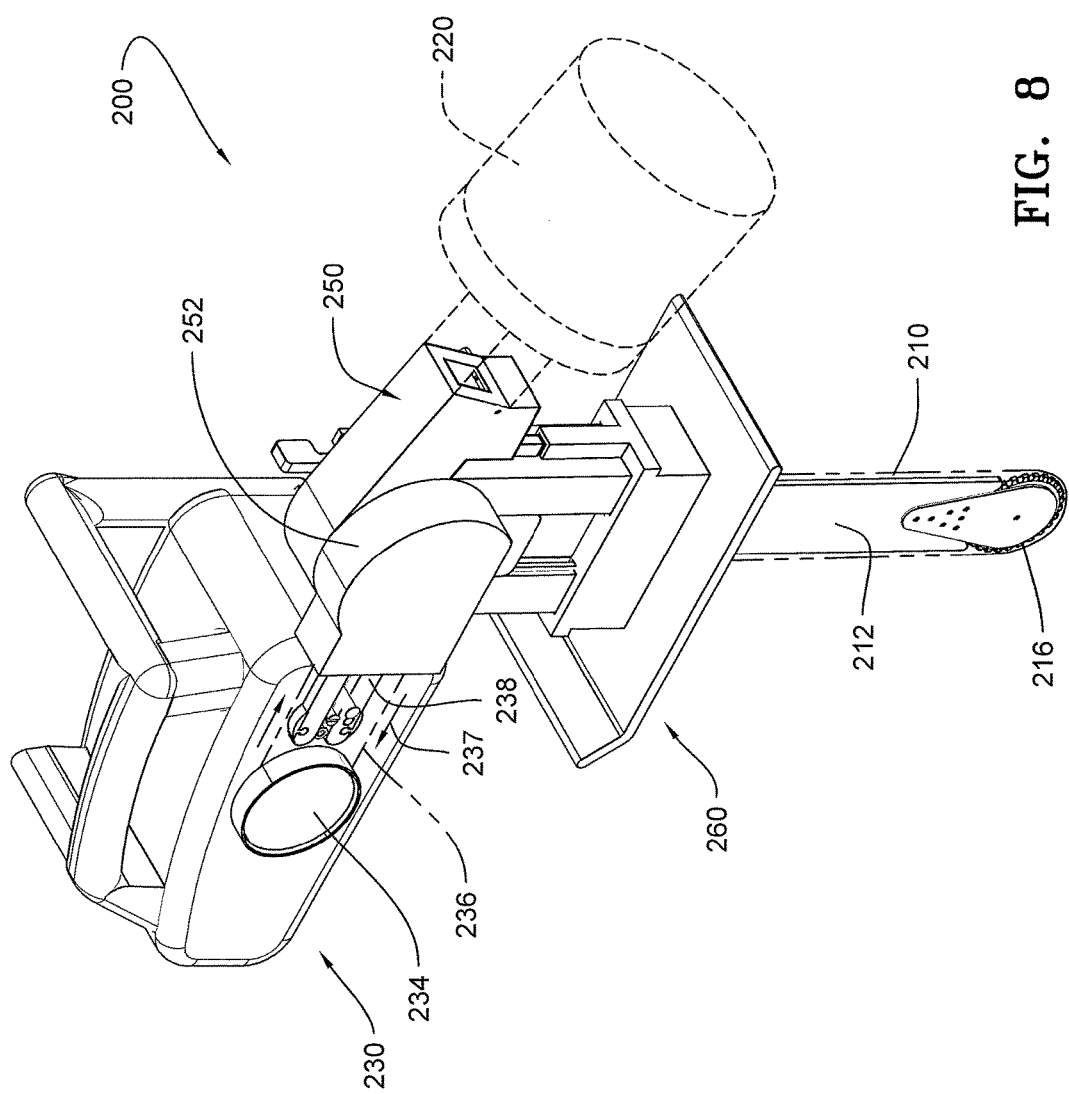
FIG. 8 is a right front upper perspective view of another embodiment of a soil sampling apparatus.
Figure 9:
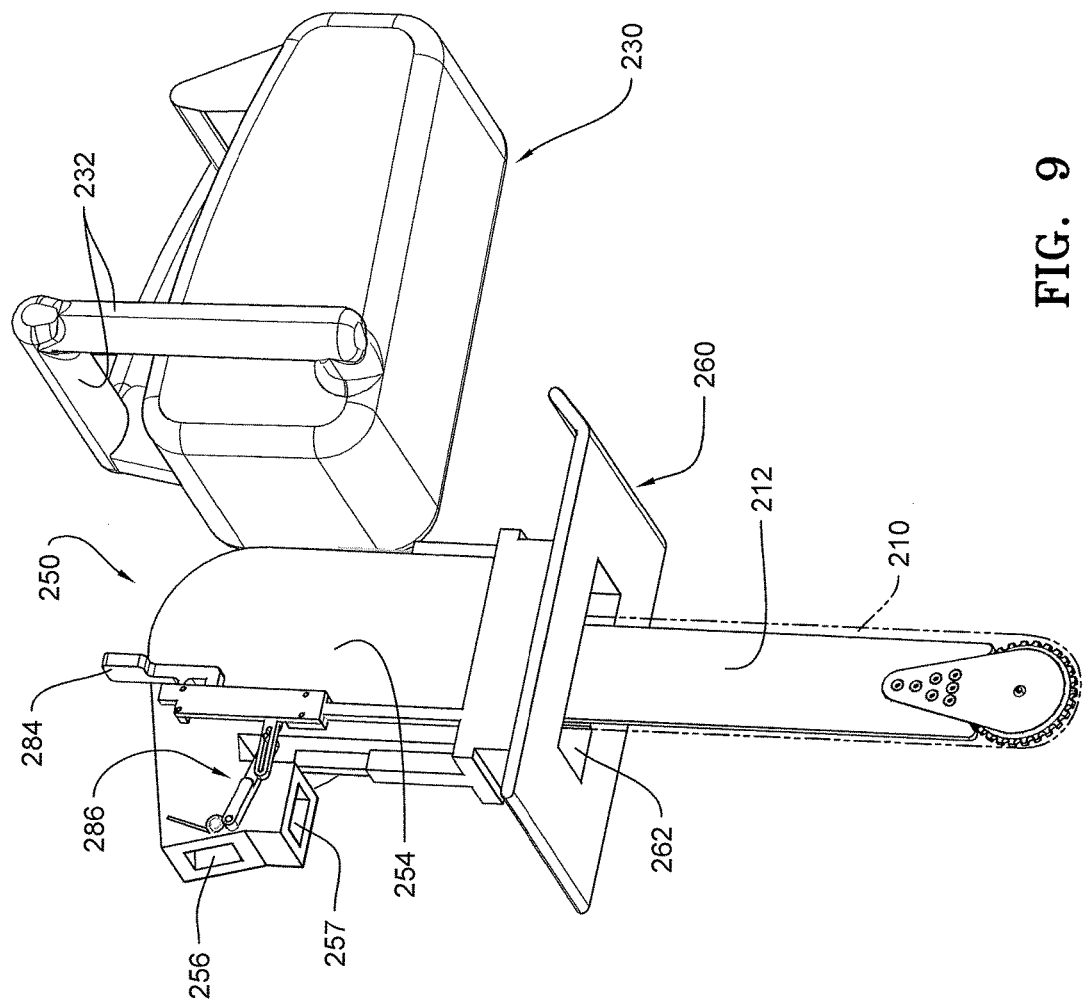
FIG. 9 is a left front lower perspective view of the soil sampling apparatus of FIG. 8.

In this embodiment, as in the previous embodiment, the soil sampling apparatus 200 includes a vertically oriented chain bar 210 supported from a main body 230. A gas powered engine or battery powered motor comprises the main body 230. The body 230 includes handles 232 for gripping by the user to push the chain chain 210 and vertically oriented guide bar 212 into the soil during the soil collecting operation (discussed later). Similar to a conventional chainsaw, one of the gripping handles 232 may include a trigger throttle (not shown). Also similar to a conventional chainsaw, the soil sampling apparatus 200 includes a drive mechanism 234. The drive mechanism 234 rotates a drive chain 236 (indicated by phantom line, but see FIG. 16 as an example). The drive chain 236 extends around the drive mechanism 234 and around a horizontal guidebar 238. At the forward end of the horizontal guidebar 238 is a drive chain sprocket 240. The drive mechanism 234 and sprocket 240 cooperate to rotate the drive chain 236 in the direction of arrow 237 as shown in FIG. 8.

Figure 11:
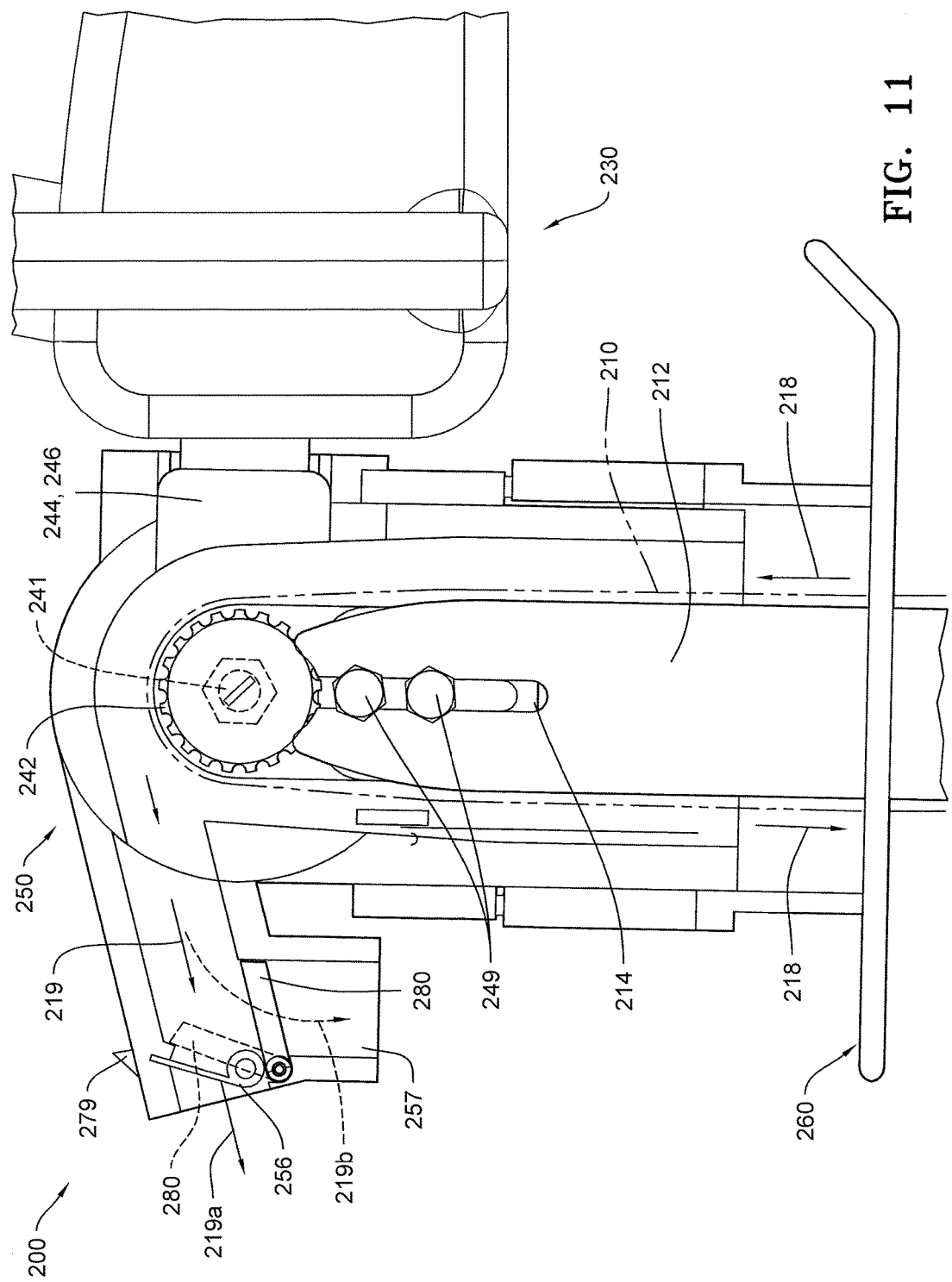
FIG. 11 is an enlarged left side elevation view of the soil sampling apparatus of FIG. 8 with the left housing panel removed to show the interior of the housing.

The drive shaft 241 rotatably couples the drive chain sprocket 240 with an upper shaving chain sprocket 242 (FIG. 11). The soil shaving chain 214 extends around the upper shaving chain sprocket 242 and around a lower shaving chain idler sprocket 216 at the opposite end of the vertical guide bar 212. The sprockets 242, 216 cooperate to rotate the shaving chain 214 around the guidebar 212 in the direction of arrow 218 (see FIG. 11).

The drive shaft 241 is rotatably supported from the main body 230 by an L-shaped bracket 244, with the horizontal leg 246 of the L-shaped bracket 244 rigidly secured to the engine body 230, such as by a threaded connector (not shown). The vertical leg 248 of the L-shaped bracket 244 serves as a mount for the vertical guidebar 212 of the chain bar 210. The vertical leg 248 of the L-shaped bracket threadably receives the threaded connectors 249 which extend through a vertical slot 214 in the vertical guidebar 212 thereby frictionally vertically and laterally restraining the vertical guidebar 212 with respect to the L-shaped bracket 244.

As best shown in FIG. 11, the upper end of the vertical guidebar 212, the drive chain sprocket 240 and the upper shaving chain sprocket 242 are received within a housing 250, comprising right and left side panels 252, 254 spaced apart by a peripheral wall 253 which define an enclosure with an open bottom. The housing 250 is likewise supported from the L-shaped bracket 244. In FIG. 11, the left housing panel 254 is removed to show the interior of the housing 150.

A foot plate 260 is supported from the base of the housing 250. The foot plate 260 includes an opening 262 through which the chain bar 210 extends. Foot slide channels 264 cooperate with a rib 266 on the housing 250 permitting the foot plate 260 to be vertically adjustable with respect to the end of the vertical guidebar 212 thereby enabling the user to set the depth of penetration of the chain bar 210 into the soil (e.g., at 12, 18 or 24 inch depths).

Figure 12:
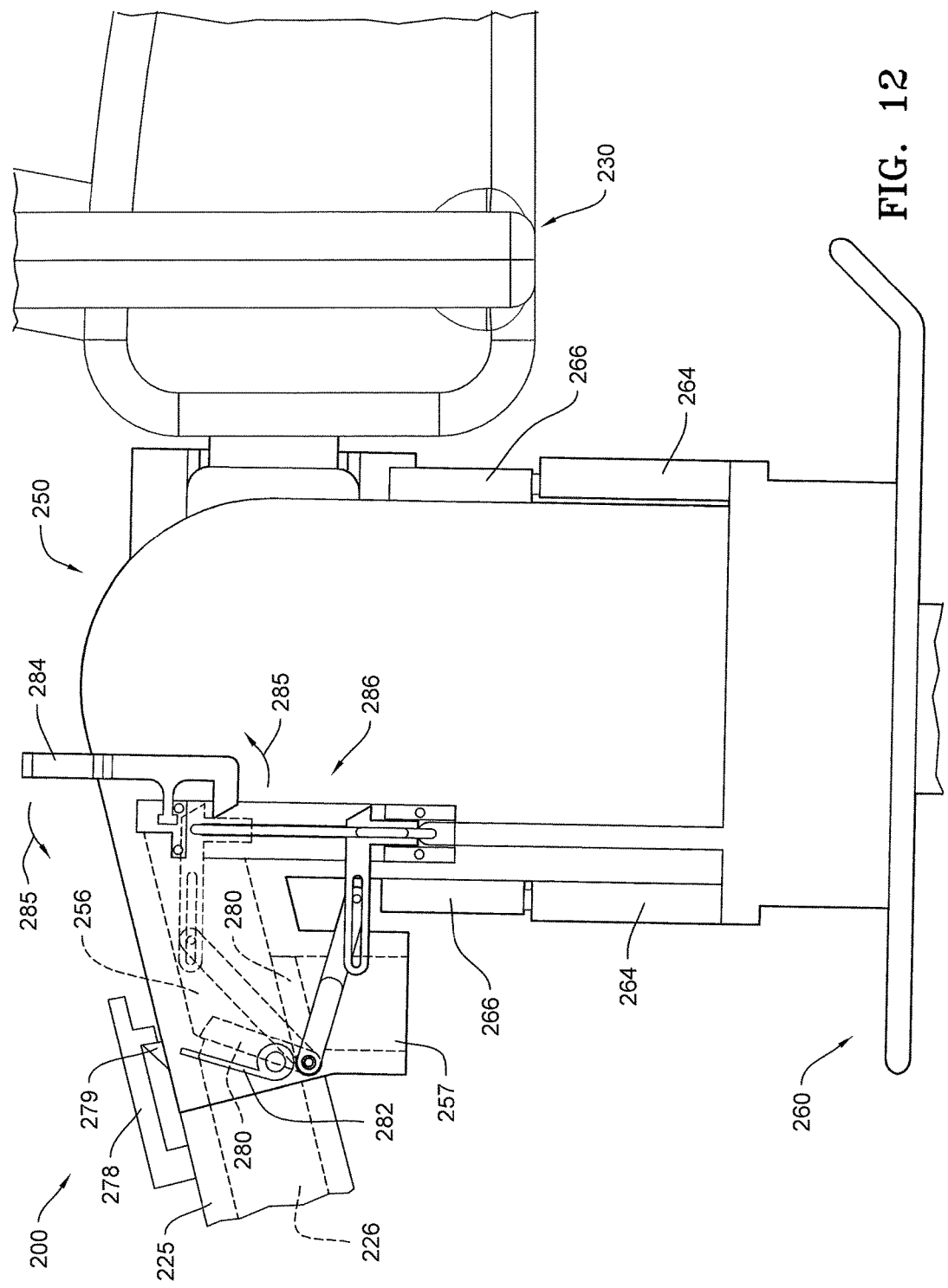
FIG. 12 is an enlarged left side elevation view of the soil sampling apparatus of FIG. 8 showing the pivotal movement of the housing gate and gate lever.
Figure 13:
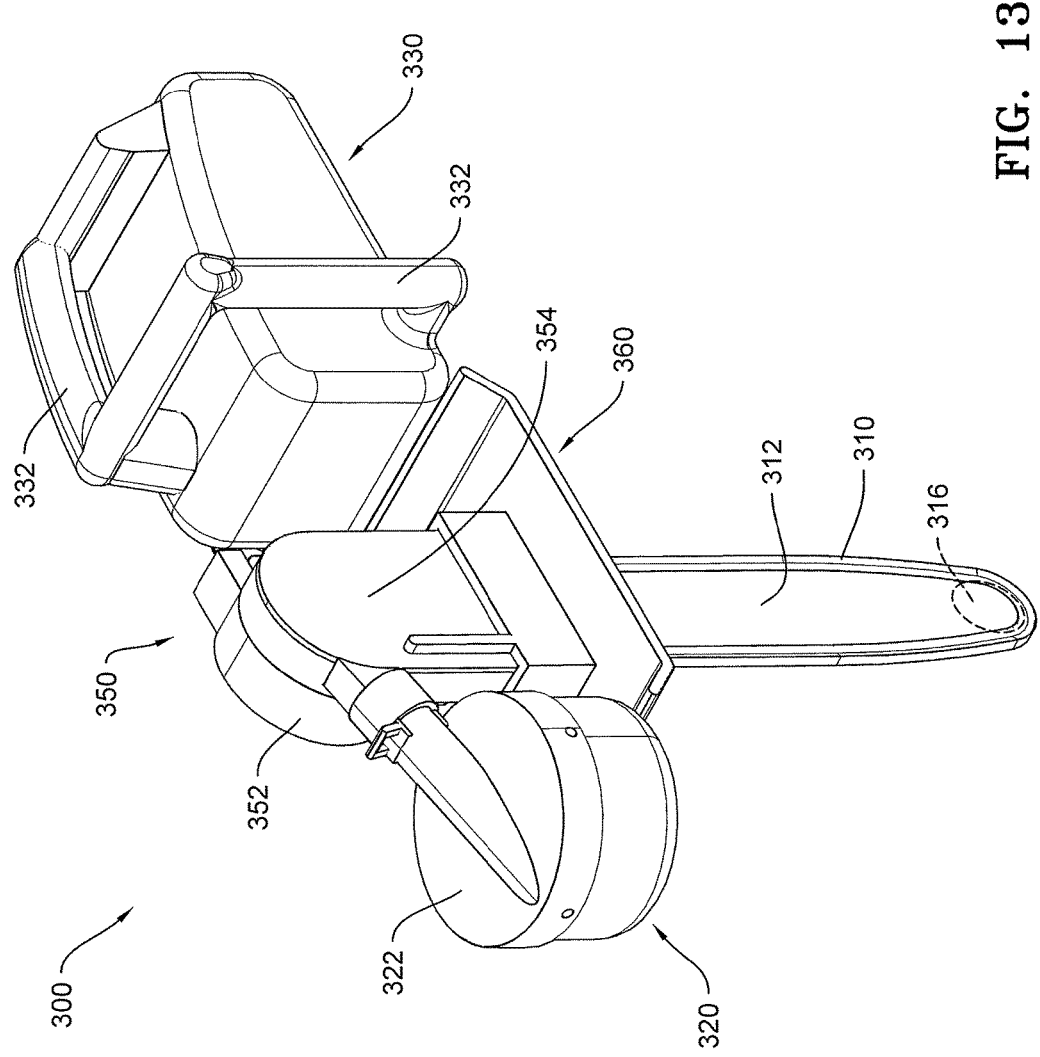
FIG. 13 is a left front upper perspective view of another embodiment of a soil sampling apparatus.
Figure 14:
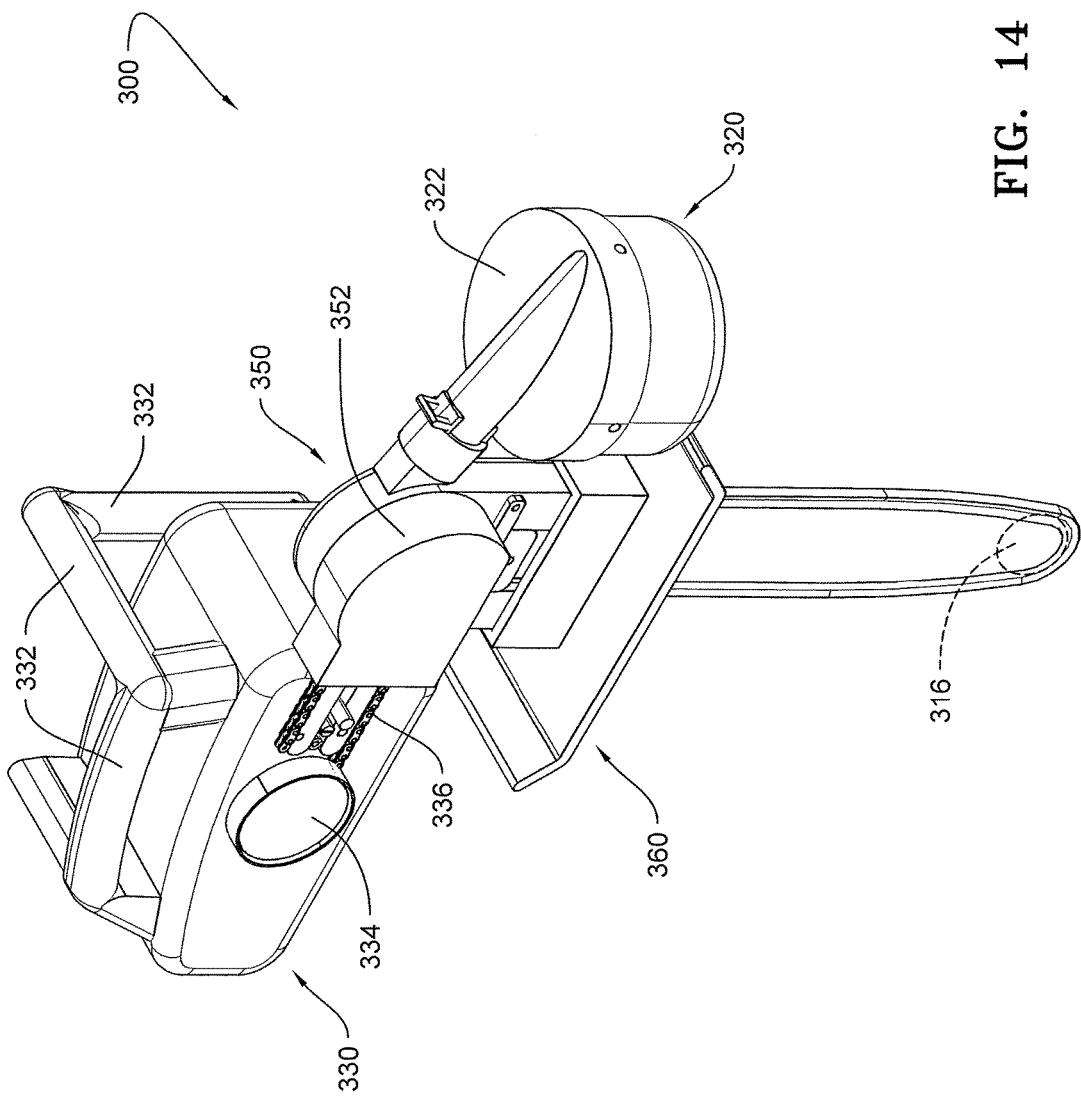
FIG. 14 is a right front upper perspective view of the soil sampling apparatus of FIG. 13.

The canister 220 and lid 222 may be the same as the canister 120 and lid 122 of the first embodiment and therefore, further discussion is not required. However, unlike the first embodiment, in the second embodiment as shown in FIG. 12, the connecting tube 225 extending from the top side of the lid 222 is rigidly mounted to the housing 250 by any suitable means. For example, the connecting tube 225 may include a resilient tab 278 that cooperates with a lip 279 on the top side of the housing 250 to secure the canister 220 to the housing 250 with the passage 226 of the connecting tube 225 and passage 256 of the housing 250 aligned.

Referring to FIGS. 11 and 12, in this embodiment, the housing 250 includes a second passage or outlet 257 through which the soil shavings may be directed by pivoting a gate 280 between open and closed positions. In the open position, the soil shavings from the soil shaving chain 214 are directed through the housing passage 256 and through the connecting tube passage 226 and into the canister 220 as indicated by arrow 219a (FIG. 11). When the gate 280 is in the closed position, the soil shavings are directed downwardly through the second passageway as 257 as indicated by the dashed arrow 219b (FIG. 11).

Figure 10:
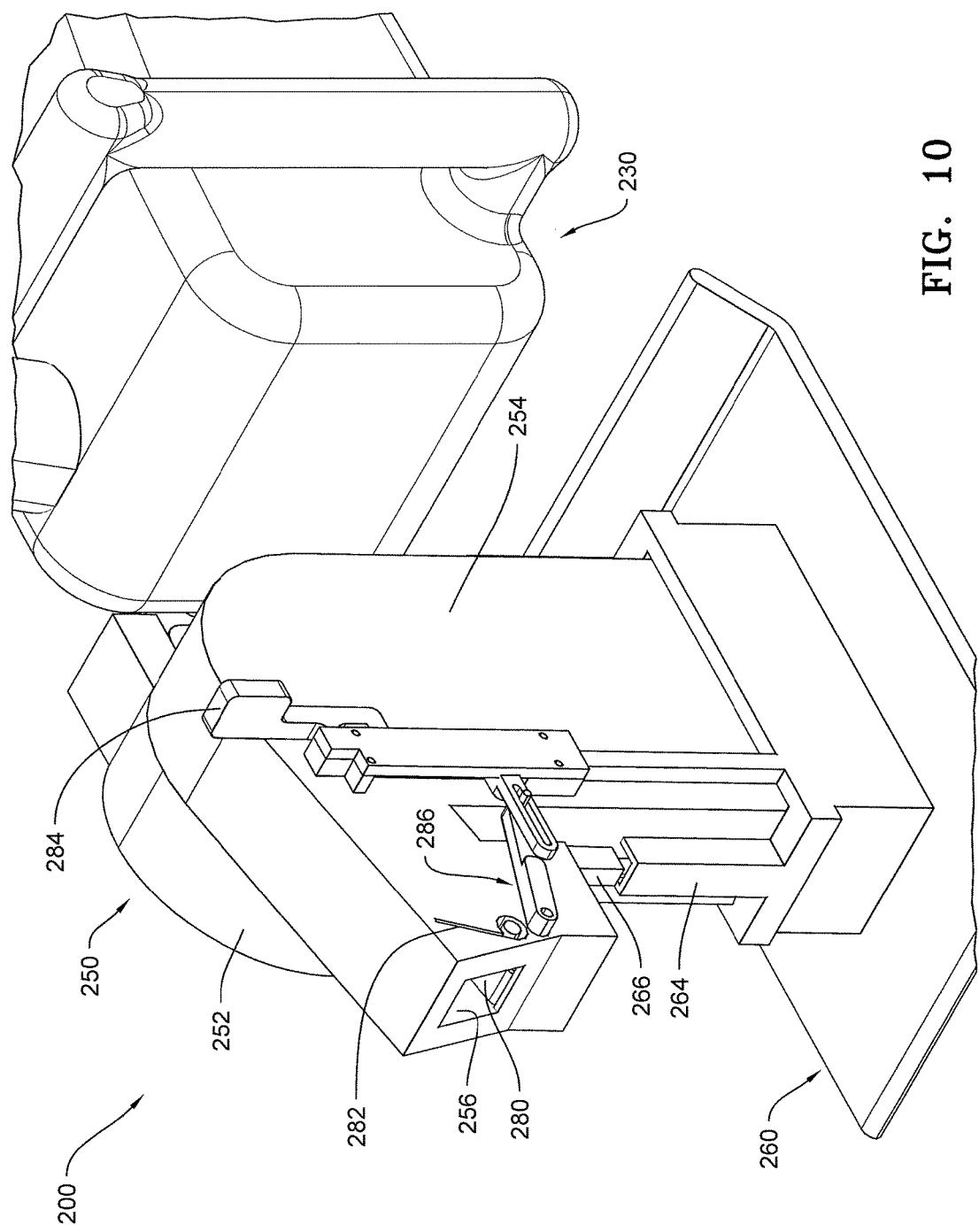
FIG. 10 is an enlarged front left perspective view of the housing of the soil sampling apparatus of FIG. 8.

The gate 280 is biased in the open position by a torsion spring 282 (FIG. 10). A release lever 284 cooperates with a mechanical linkage 286 for releasing the gate 280 from the closed position. An embodiment of the mechanical linkage 286 is illustrated in FIG. 12 showing the position of the mechanical linkage 286 in dashed lines when the gate 280 is closed and in solid lines when the gate 280 is opened by pushing the release lever 284 forwardly as indicated by arrow 285. It should be appreciated that when pushing the lever 284 forwardly as indicated by arrow 285, the lower projection 287 of the lever 284 is moved out of engagement with the bar 288 releasing the mechanical linkage 286. The bias of the torsion spring 282 forces the gate 280 to the closed position as the linkage 286 moves downwardly from the upper position (dashed lines in FIG. 12) to the lower position (solid lines in FIG. 12).

In use, the gate 280 is moved to the closed position causing the soil shavings to be discharged through the second outlet 257 of the housing 250. When the desired sampling depth is reached, the user pushes the release lever 284 forwardly causing the gate 280 to be opened so that the soil shavings may enter the canister 220. By drawing the chain bar 210 rearward as the soil shaving chain 214 rotates, the soil is carried up into the housing 250 by the teeth 215 on the soil shaving chain 214. When the teeth 215 pass over the upper sprocket 242, the soil shavings carried by the teeth are flung or discharged in the direction of arrow 219 through the housing outlet 256 and through the passage 226 and into the canister 220.

It should also be appreciated that the gate may be positioned such that it is only partially opened, thereby collecting only a percentage of soil shavings so as to obtain soil samples over a broader area at the desired depth, with the remainder of the soil shavings being discharged through the partially opened second passage 257.

Additionally, it should also be appreciated that multiple canisters 220 may be attached to the housing 250 at one time for separately collecting the soil shavings at different depths without having to stop and swap out containers. For example, a first container 220a may be mounted to the first passage 256 as previously described and a second container 220b may be mounted to the second passage 257 in a similar manner. In operation, the gate 280 may be closed so the soil shavings are directed to the second canister 320b through the second passage 257 at a first desired sample depth (e.g., at a 12 inch depth). When it is desired to collect soil shavings at a second depth (e.g., 24 inches), the lever 284 may be released to open the gate 280 permitting soil shavings to pass through the first passage 256 and into the first container 320a while blocking the second passage 257.

FIGS. 13-16 illustrate another alternative soil sampling apparatus 300 which is substantially similar to the first and second embodiments, except for the manner in which the canister is attached to the housing.

Figure 16:
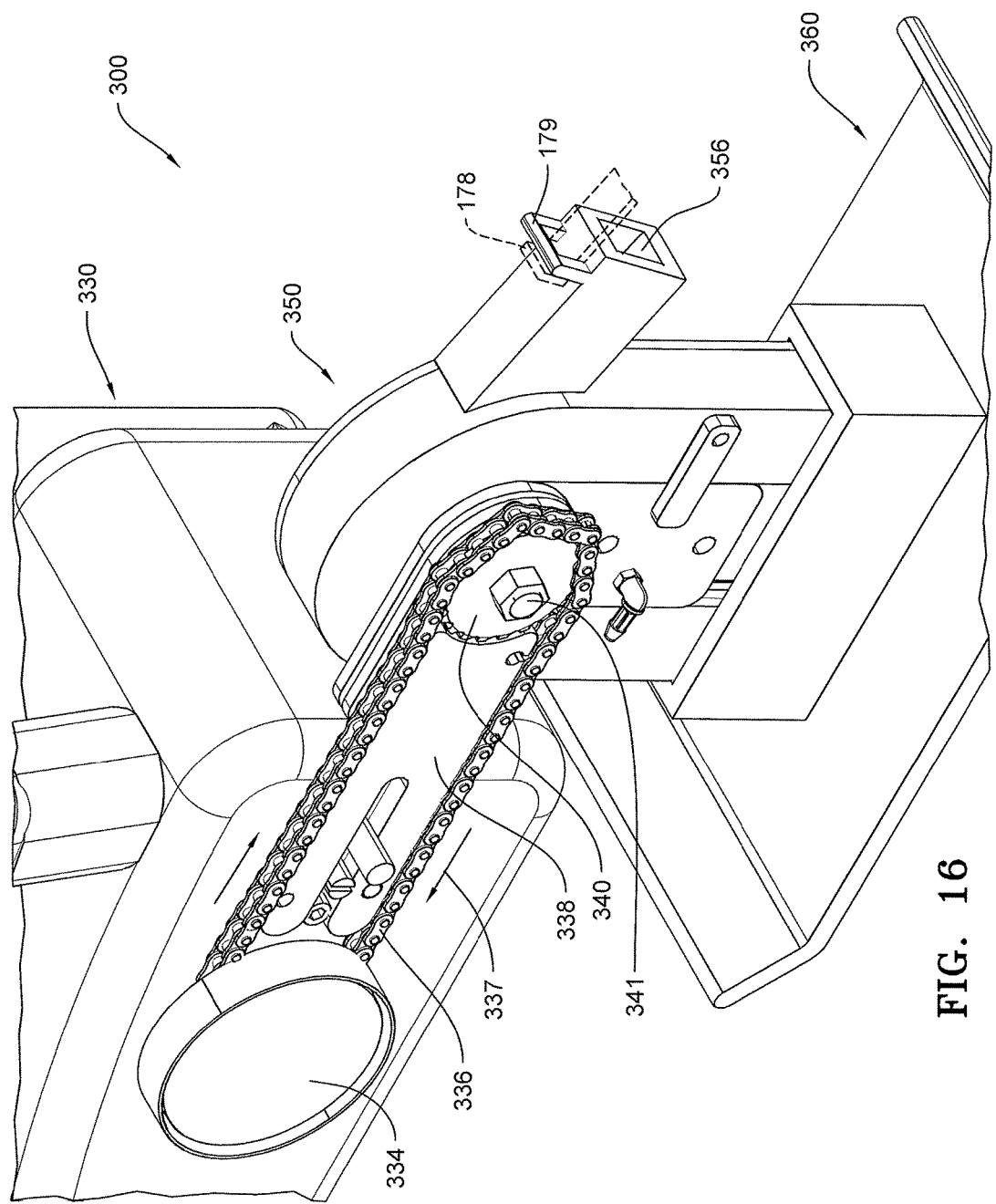
FIG. 16 is an enlarged right front perspective view of FIG. 13 with the right sidewall of the housing removed to show the interior of the housing.

In this embodiment, as in the previous embodiment, the soil sampling apparatus 300 includes a vertically oriented chain bar 310 supported by a main body 330. The main body 330 comprises a gas powered engine or battery powered motor. The body 330 includes handles 332 for gripping by the user to push the chain chain 310 and vertically oriented guide bar 312 into the soil during the soil collecting operation (discussed later). Similar to a conventional chainsaw, one of the gripping handles 332 may include a trigger throttle (not shown). Also similar to a conventional chainsaw, the soil sampling apparatus 300 includes a drive mechanism 334. The drive mechanism 334 which rotates a drive chain 336 (FIG. 16). The drive chain 336 extends around the drive mechanism 334 and around a horizontal guidebar 338. At the forward end of the guidebar 338 is a drive chain sprocket 340. The drive mechanism 334 and sprocket 340 cooperate to rotate the drive chain 336 in the direction of arrow 337 as shown in FIG. 16.

Figure 15:
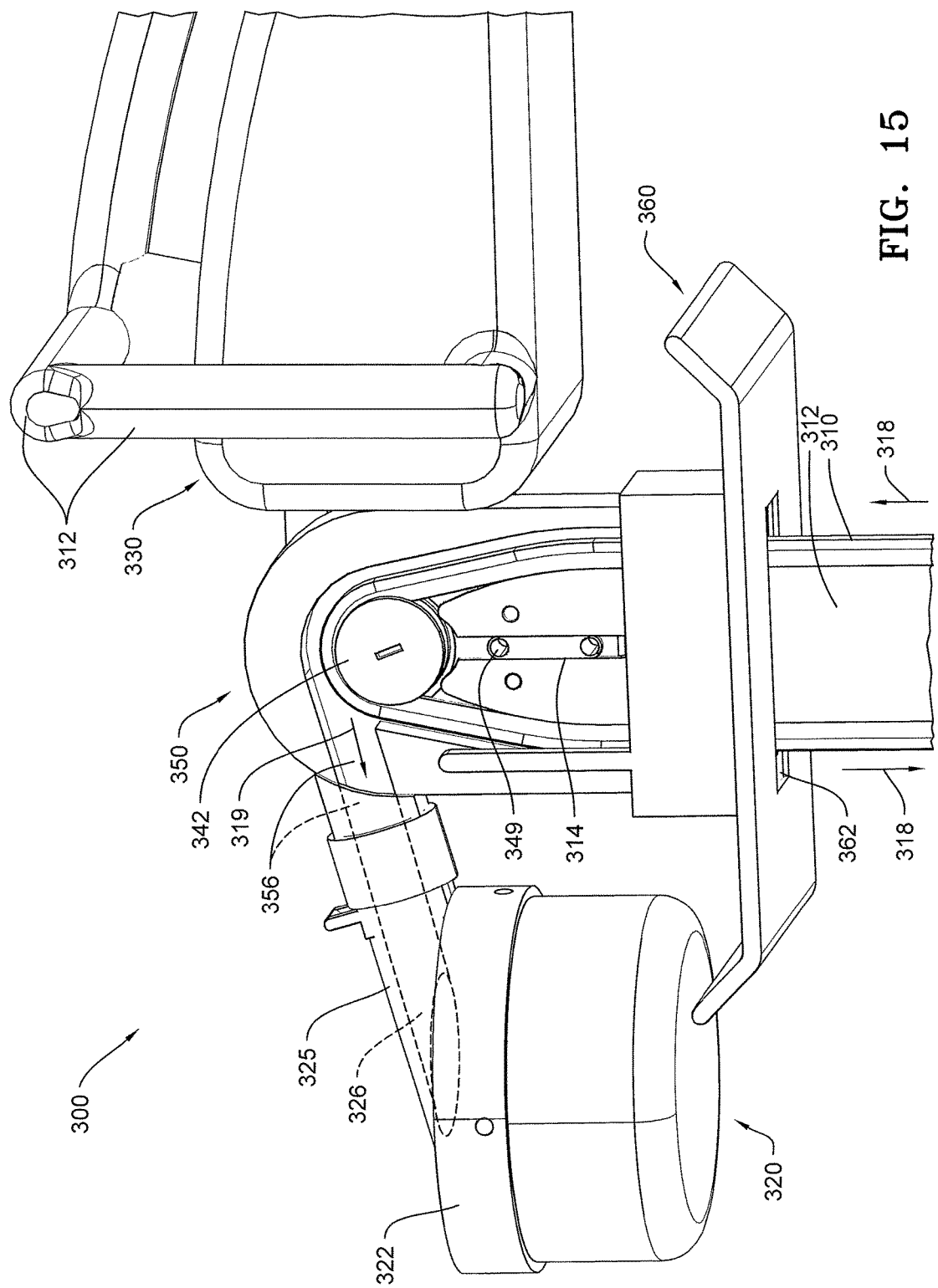
FIG. 15 is an enlarged side elevation view of the housing of the soil sampling apparatus of FIG. 15 with the left sidewall removed to show the interior of the housing.

The drive shaft 341 rotatably couples the drive chain sprocket 340 with an upper shaving chain sprocket 342 (FIG. 15). The shaving chain 314 extends around the upper shaving chain sprocket 342 and around a lower shaving chain idler sprocket 316 at the opposite end of the vertical guide bar 312. The sprockets 342, 316 cooperate to rotate the shaving chain 314 around the guidebar 312 in the direction of arrow 318 (see FIG. 15).

The drive shaft 341 is rotatably supported from the main body 330 by an L-shaped bracket 344, with the horizontal leg 346 of the L-shaped bracket 344 rigidly secured to the body 330, such as by a threaded connector (not shown). The vertical leg 348 of the L-shaped bracket 344 serves as a mount for the vertical guidebar 312. The vertical leg 348 of the L-shaped bracket threadably receives the threaded connectors 349 which extend through a vertical slot 314 in the vertical guidebar 312 thereby frictionally vertically and laterally restraining the vertical guidebar 312 with respect to the L-shaped bracket 344.

As best shown in FIGS. 15 and 16, the upper end of the vertical guidebar 312, the drive chain sprocket 340 and the upper shaving chain sprocket 342 are received within a housing 350, comprising left and right housing panels 352, 354 secured together by a plurality of threaded connectors (not shown). The housing 350 is likewise supported from the L-shaped bracket 344. In FIG. 15, the left housing panel 354 is removed to show the interior of the housing 350. In FIG. 16, the right housing panel 352 is removed to show the interior of the housing 350.

A foot plate 360 is supported from the base of the housing 350. The foot plate 360 includes an opening 362 through which the chain bar 310 extends. The foot plate 360 may be vertically adjustable with respect to the end of the vertical guidebar 312 thereby enabling the user to set the depth of penetration of the chain bar 310 into the soil (e.g., at 12, 18 or 24 inch depths).

The canister 320 and lid 322 may utilize the same type of peg and locking slot configuration (124, 123) described in connection with the first embodiment. However, unlike the first embodiment, in this third embodiment, the connecting tube 325 extending from the top side of the lid 322 is rigidly mounted to the housing 350 by any suitable means. For example, the connecting tube 325 may include a resilient tab 378 that cooperates with a lip 379 on the top side of the housing 350 to secure the canister 320 to the housing 350 with the passage 326 of the connecting tube 325 and passage 356 of the housing 350 aligned.

In use, the canister 320 is removed from the housing 350 allowing the soil shavings to be discharged through the outlet 356 of the housing 350. When the desired sampling depth is reached, the user attaches the canister 320 to the housing 350 with the passages 326 and 356 aligned so that soil shavings may enter the canister 320. By drawing the chain bar 310 rearward as the soil shaving chain 314 rotates, the soil shavings are carried up into the housing 350 by the teeth 315 on the soil shaving chain 314. When the teeth 315 pass over the upper shaving chain sprocket 342, the soil shavings carried by the teeth are flung or discharged in the direction of arrow 319 through the housing outlet 356 and through the passage 326 and into the canister 320.

Figure 17:
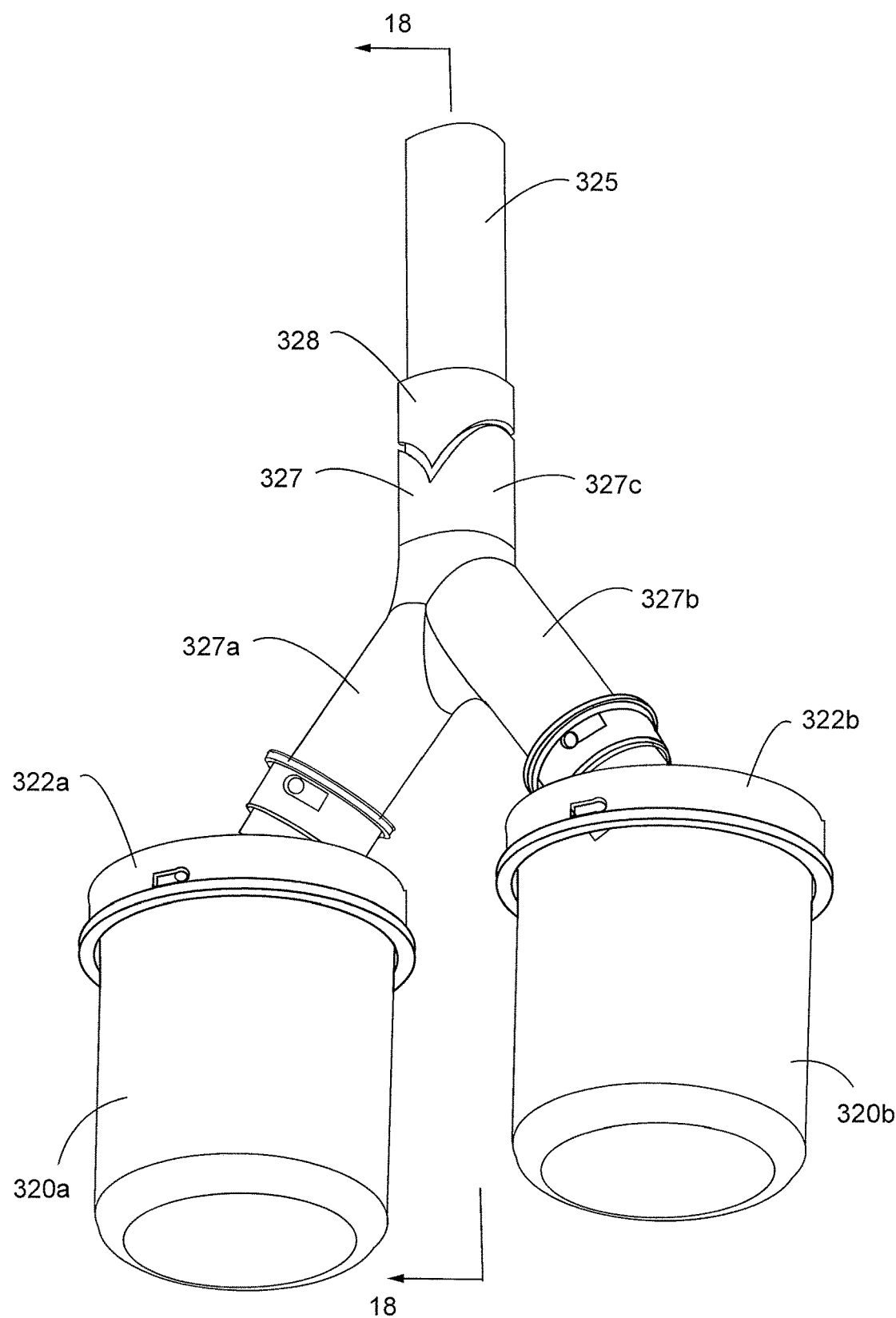
FIG. 17 is an embodiment of a dual canister assembly for use with the soil sampling apparatus of FIG. 13.
Figure 18:
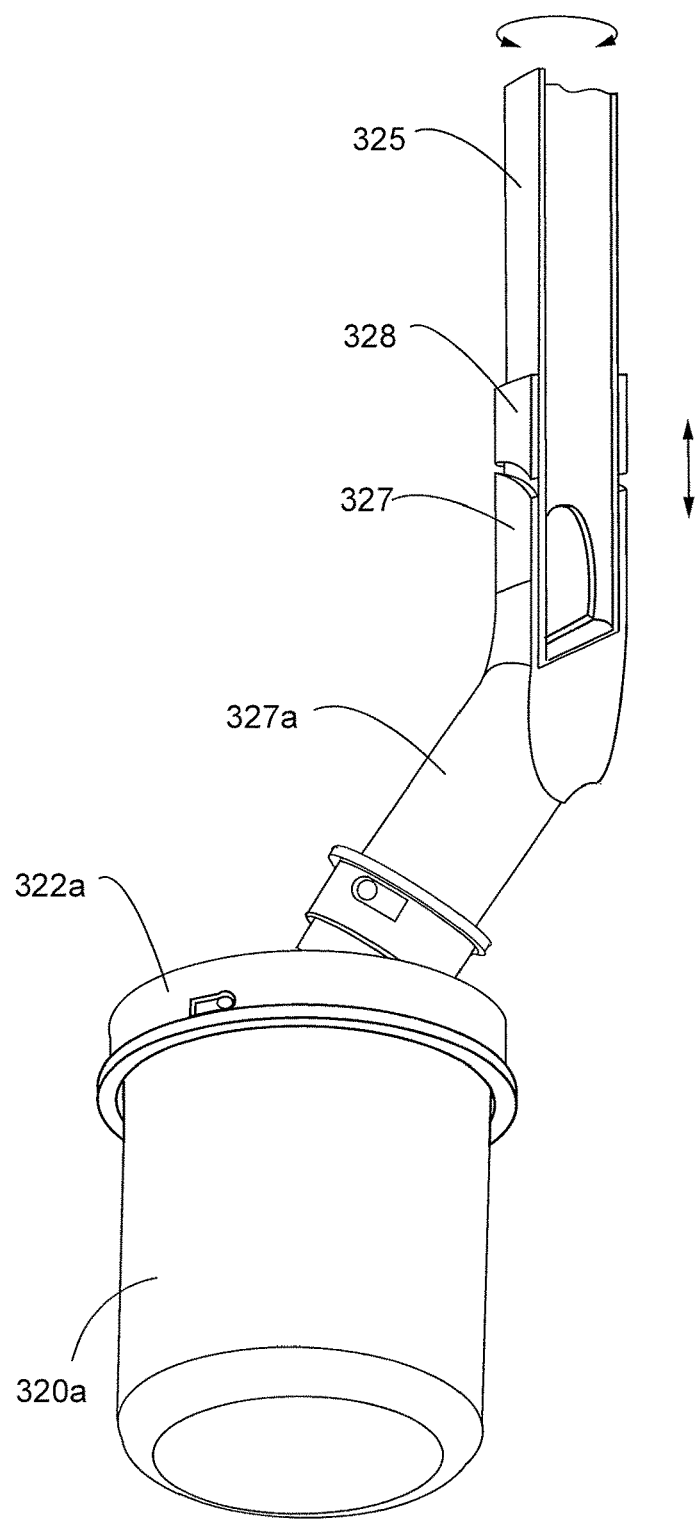
FIG. 18 is a cross-sectional view of the dual canister assembly as viewed along lines 18-18 of FIG. 17.

As with the second embodiment, multiple canisters may also be used with this third embodiment to collect the soil shavings quickly and conveniently in isolated canisters 320a, 320b as shown in FIG. 17. In this embodiment, a Y-tube 327 includes diverging tube legs 327a, 327b and an inlet tub 327c. The connecting tube 325 is rotatably received within the inlet tube 327c. The connecting tube 325 has a closed end and only one opening 326 in its sidewall. A stub sleeve 328 which is fixedly attached to the connecting tube 325. The inlet tube 327c of the Y-tube 327 is keyed at two points 180 degrees apart so as to matingly align with a complimentary rearward end of the stub sleeve 328. In use the soil passes through connecting tube 325 and through the opening 326 aligned with the first diverging tube leg 327a and into the associated first canister 320a. When it is desired to collect the soil in the second canister 320b, the Y-tube 327 is pulled rearwardly and rotated 180 degrees so as to matingly align the keyed inlet tube 327c with the opposing keyed rearward end of the stub sleeve 328 and thereby aligning the opening 326 with the second diverging tube leg 327b so the soil shavings can pass into the second canister 320b.

It should be appreciated that in each of the embodiments, the soil shavings are quickly and conveniently collected and isolated in the canisters 120, 220, 320 without the need for additional handling or transferring of the soil shavings and the soil shavings collected in the isolated canisters is representative of the soil profile at the sampling depth of interest. Additionally, due to the action of the soil shaving chain 114, 214, 314 the soil shavings that are discharged from the chain into the canisters is mixed, macerated and free of large clumps. The soil shavings samples collected in the canisters can then be taken to a soil lab for analysis or the soil shavings may be tested using a portable soil testing apparatus and method as disclosed in U.S. Publication No. 2014/0345394, which is incorporated herein in its entirety by reference.

Figure 19:
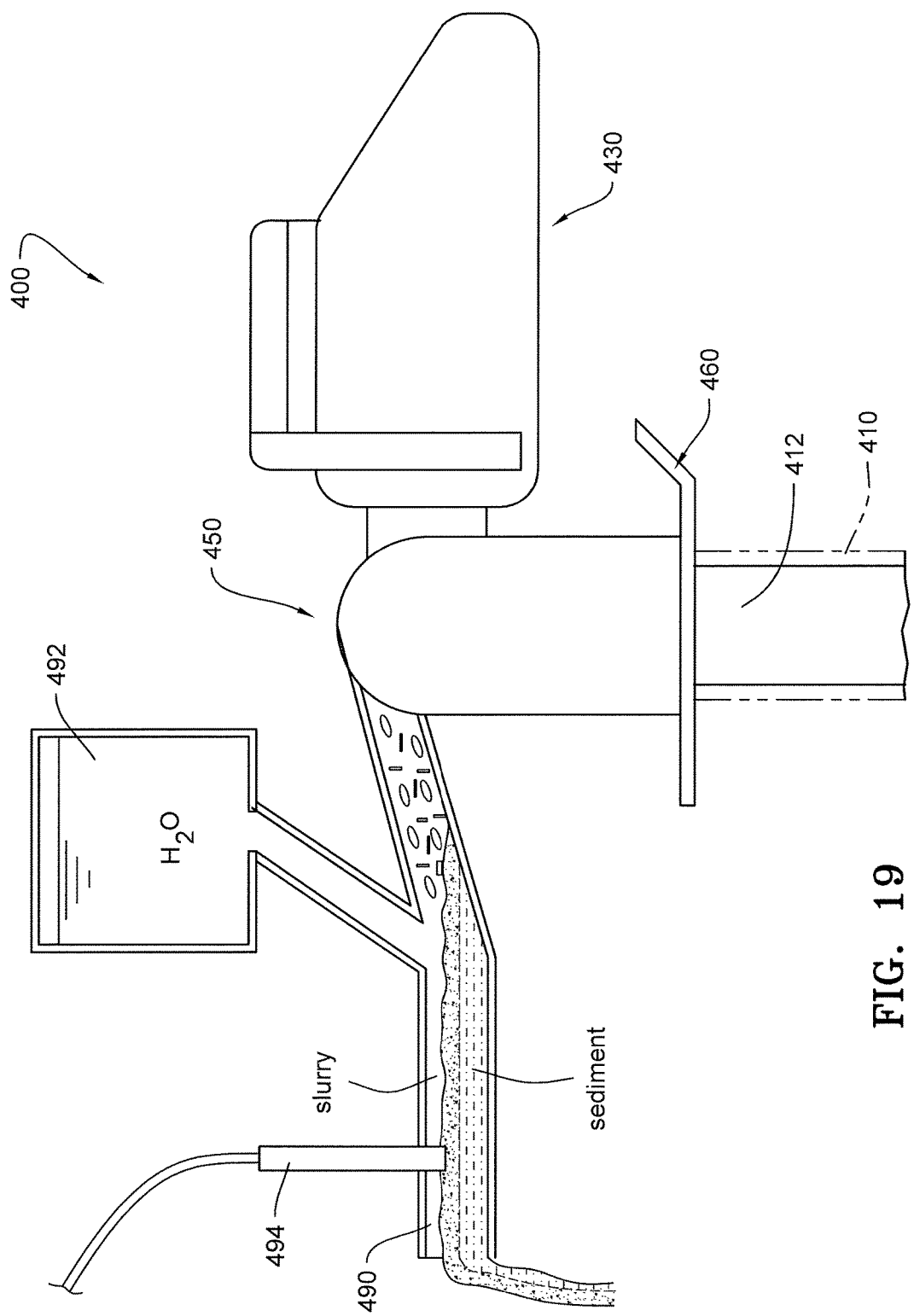
FIG. 19 is a schematic illustration of another embodiment of the soil sampling apparatus comprising a continuous flow system.

FIG. 19 schematically illustrates yet another embodiment of a soil sampling apparatus comprising a continuous flow soil sampling system 400. In this embodiment, the same components as previously described with respect to the other embodiments are utilized except that the canisters are eliminated and instead the soil shavings discharged from the soil shaving chain enter a mixing chamber 490 extending from the housing 450. A water source 492 (preferably containing deionized water) is in fluid communication with the mixing chamber 490. The water may be communicated from the water source to the mixing chamber 490 via gravity, a pump or otherwise under pressure from a pressure source. The soil is mixed with the water within the mixing chamber 490 to produce a slurry. A sensor 494 may be positioned within the mixing chamber to detect the soil characteristics of the soil sample slurry. The continuous flow soil sampling embodiment 400 may be combined with the portable soil testing apparatus and method as disclosed in U.S. Publication No. 2014/0345394, previously incorporated herein by reference. The mixing chamber 490 may incorporate an auger (not shown) or other means of mixing the sediment with the water to produce the slurry and to assist in moving the sediment out of the mixing chamber.

Each of the embodiments of the soil sampling systems 100, 200, 300, 400 may be equipped with one or more sensors to sense soil characteristics associated with the soil shaving sample collected and to transmit the parameters to a remote server or to a software application on a mobile device using Bluetooth, cellular or other wireless communication. One such sensor may be a nitrogen sensor to detect nitrogen content of the soil. The guide bar 112, 212, 312, 412 may also be equipped with a strain gauge to determine soil compaction. The canisters 120, 220, 320, 420 may be equipped with a level sensor to detect when a certain amount of soil is collected within the canisters. The systems 100,

200, 300, 400 may include a proximity sensor to determine and indicate the depth of penetration of the guidebar 112, 212, 312, 412 into the soil surface and an accelerometer to determine when the guidebar is inserted into the soil. The systems 100, 200, 300, 400 may also include dual cameras to create a 3D profile of the soil. The systems 100, 200, 300, 400 may also include RGB sensors to identify soil type, correlated to soil moisture level. The systems 100, 200, 300, 400 may also include or incorporate soil probes 500 as described below. These sensed characteristics may be displayed on a monitor or mobile device for viewing by the user, for example, wherein the GPS coordinate locations and sample depth from the sensors are automatically uploaded into a mobile device application and displayed on the mobile device screen as illustrated in FIG. 20.

Figure 21:
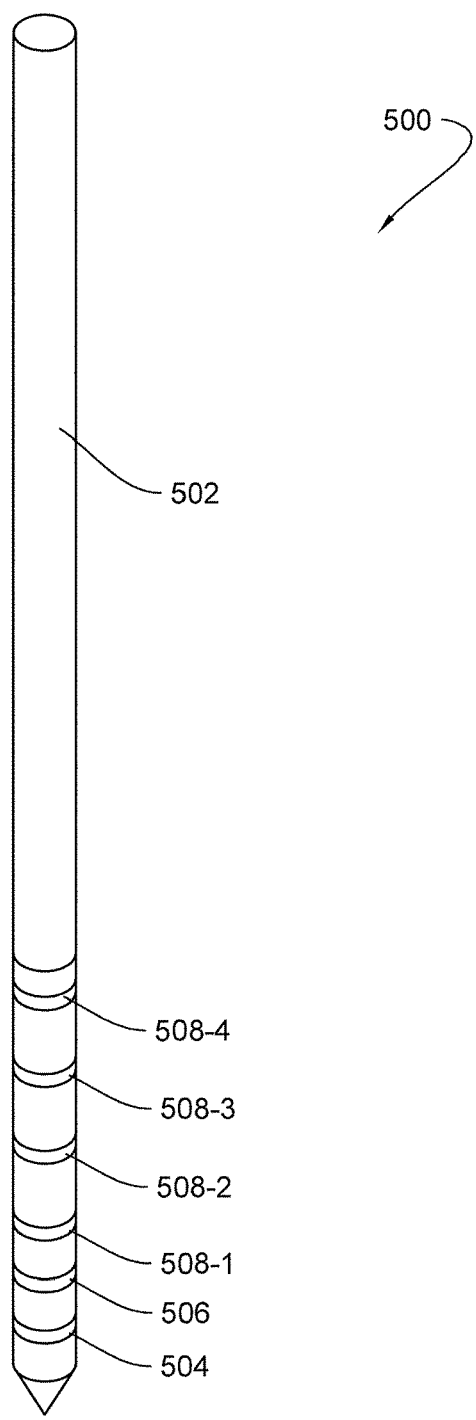
FIG. 21 is an embodiment of a soil probe.

A soil probe 500 as illustrated in FIG. 21 may be secured to the foot plate 160, 260, 360, 460 for penetrating into the soil as the cutting chain cuts into the soil. Alternatively, the soil probe 500 may be inserted into or be positioned within the canisters 120, 220, 320 in each of the embodiments or the probe 500 may be positioned within the passageway 156, 256, 356, 456 of the housing 150, 250, 350, 450 of the various embodiments to sense soil parameters as the soil shavings are discharged from the chain. In one embodiment the soil probe includes a rod 502 of non-electrically conductive material with a plurality of spaced rings. The first ring may be a heating ring 504. The second ring may be a temperature sensing ring 506. The remaining rings may be electrically conductive rings 508-1, 508-2, 508-3, 508-4 for measuring electrical conductivity of the soil. For example, an electrical current may be directed through the outer rings 508-1, 508-4 and the voltage change may be sensed between the two middle rings 508-2, 508-3. The electrical conductivity of the soil may be correlated to clay content, cation exchange capacity, organic Carbon, silt content, soil moisture and sand content of the soil. The soil temperature ring 504 may be used to detect the soil temperature. The heating ring 504 and temperature sensor ring 506 may be used cooperatively to calibrate for drift in the electrical conductivity measurement. Additionally, a strain gauge (not shown) may be attached to the probe 500 to measure soil compaction as the probe is forced into the soil.

Various embodiments of the invention have been described above for purposes of illustrating the details thereof and to enable one of ordinary skill in the art to make and use the invention. The details and features of the disclosed embodiment are not intended to be limiting, as many variations and modifications will be readily apparent to those of skill in the art. Accordingly, the scope of the present disclosure is intended to be interpreted broadly and to include all variations and modifications coming within the scope and spirit of the appended claims.

The invention claimed is:

1. A soil sampling apparatus, comprising:
a housing having spaced side panels and a peripheral wall;
a discharge opening in the wall;
a continuous soil shaving chain positioned at least in part within the enclosure of the housing;
a drive mechanism coupled to a power source and configured to rotate the continuous soil shaving chain around while penetrating a soil surface;
a connection tube in communication with the discharge opening, the connection tube having an outlet, whereby as the soil shaving chain penetrates the soil, soil shavings discharged from the continuous soil shaving chain pass through the discharge opening of the housing, into the connection tube and out through the outlet of the connection tube.

2. The soil sampling apparatus of claim 1, further comprising:
at least one soil collection canister in communication with an outlet of the connection tube, whereby the discharged soil shavings exiting the outlet of the connection tube are collected in the at least one collection canister.

3. The soil sampling apparatus of claim 2, wherein the at least one soil collection canister comprises a canister body and a canister lid, the canister body being removable from the canister lid.

4. The soil sampling apparatus of claim 2, wherein the at least one soil collection canister is pivotally movable with respect to the connection tube such that the at least one soil collection canister is pivotally movable into and out of communication with the discharge opening.

5. The soil sampling apparatus of claim 2, wherein the at least one canister comprises a first canister and a second canister, the apparatus further comprising:
a Y-member having an inlet tube and diverging first and second tube legs, the inlet tube having an opening in communication with the outlet of the connection tube, the first canister attached to the first tube leg, the second canister attached to the second tube leg;
a diverter rotatable to selectively direct the discharged soil shavings between the first and second canisters.

6. The soil sampling apparatus of claim 2, wherein the at least one soil collection canister includes a sensor to detect an amount of discharged soil shavings collected in the at least one soil collection canister.

7. The soil sampling apparatus of claim 2, further comprising:
a soil probe disposed in the at least one soil collection canister, the soil probe having a plurality of spaced rings, wherein a first of the plurality of spaced rings includes a temperature sensing ring configured to detect soil temperature, and wherein other of the plurality of spaced rings are configured to detect electrical conductivity of the soil.

8. The soil sampling apparatus of claim 1, further comprising:
a vertically adjustable foot plate for setting a penetration depth of the continuous soil shaving chain into the soil.

9. The soil sampling apparatus of claim 1, wherein the connection tube includes a bypass opening and a gate disposed between the discharge opening and the outlet, the gate pivotally movable to at least partially block the outlet so as to direct at least some of the discharged soil shavings through the bypass opening.

10. The soil sampling apparatus of claim 1, wherein the connection tube comprises a mixing chamber, the mixing chamber in fluid communication with a water source, whereby the discharged soil shavings passing into the mixing chamber of the connection tube mix with water from the water source producing a soil slurry, the apparatus further comprising:
a sensor disposed to detect soil characteristics of the soil slurry within the mixing chamber.

11. The soil sampling apparatus of claim 10, wherein the sensor is in signal communication with a portable soil testing apparatus.

12. The soil sampling apparatus of claim 1, further comprising: a guide bar having a first end and a second end, the first end received within the enclosure of the housing, the second end extending from the housing through an open bottom end, the continuous soil shaving chain disposed around the guide bar.

13. The soil sampling apparatus of claim 12, further comprising:
a proximity sensor disposed in relation to the guide bar to detect a depth of penetration into the soil of the guide bar.

14. The soil sampling apparatus of claim 12, further comprising:
a soil probe secured to a foot plate to penetrate the soil as the guide bar penetrates the soil, the soil probe having a plurality of spaced rings, wherein a first of the plurality of spaced rings includes a temperature sensing ring configured to detect soil temperature, and wherein other of the plurality of spaced rings are configured to detect electrical conductivity of the soil.

15. The soil sampling apparatus of claim 12, further comprising:
a main body supporting the guide bar, the main body having handles for gripping by a user when supporting the main body and guide bar above a soil surface and for pushing the guide bar into the soil surface during use.

16. A method of sampling soil, comprising:
generating soil shavings using a soil shaving chain;
directing the soil shavings into mixing chamber for collection;
with a sensor disposed in the mixing chamber, sensing soil characteristics of the collection of soil shavings.

17. The method of claim 16, wherein the sensor is a nitrogen sensor.

18. The method of claim 16, wherein the mixing chamber is in fluid communication with a water source, wherein water from the water source and the collection of soil shavings produce a soil slurry in the mixing chamber, the sensor detecting nitrogen content of the soil slurry.

19. A method of sampling soil, comprising:
generating soil shavings using a soil shaving chain;
directing the soil shavings into a canister for collection, said canister having a canister body and a canister lid, the canister body being removable from the canister lid;
with a sensor disposed in the canister, sensing soil characteristics of the collection of soil shavings.

* * * * *